United States Patent [19]

Xu

[11] Patent Number: 5,766,896
[45] Date of Patent: Jun. 16, 1998

[54] METHOD OF PRODUCING IODINE BY USE OF A COPPER CONTAINING OXIDASE ENZYME

[75] Inventor: Feng Xu, Woodland, Calif.

[73] Assignee: Novo Nordisk Biotech Inc., Davis, Calif.

[21] Appl. No.: 343,308

[22] Filed: Nov. 22, 1994

[51] Int. Cl.$^6$ ............................................. C12P 3/00
[52] U.S. Cl. ................................. 435/168; 435/189
[58] Field of Search ............................. 435/190, 244, 435/168, 189

[56] References Cited

U.S. PATENT DOCUMENTS

| | | | |
|---|---|---|---|
| 4,282,324 | 8/1981 | Neidleman et al. | 435/168 |
| 4,576,817 | 3/1986 | Montgomery | 424/94 |
| 4,588,586 | 5/1986 | Kessler et al. | 424/94 |
| 4,617,190 | 10/1986 | Montgomery | 426/61 |
| 4,775,638 | 10/1988 | Haisma | 436/547 |
| 4,937,072 | 6/1990 | Kessler et al. | 424/94.4 |
| 4,996,146 | 2/1991 | Kessler | 435/28 |
| 5,055,287 | 10/1991 | Kessler | 424/7.1 |
| 5,169,455 | 12/1992 | Kessler | 134/42 |
| 5,227,161 | 7/1993 | Kessler | 424/94.4 |
| 5,480,801 | 1/1996 | Wahleithner | 435/254.2 |

OTHER PUBLICATIONS

Nellaiappau et al., *Parasitology*, 99:403–407, 1989.

*Primary Examiner*—Irene Marx
*Attorney, Agent, or Firm*—Steve T. Zelson; Elias J. Lambiris

[57] ABSTRACT

The present invention relates to a method for oxidation of iodide which comprises contacting, in an aqueous solution, a copper-containing oxidaze enzyme and a source of ionic iodide($I^-$), for a time and under conditions sufficient to permit the conversion of ionic iodide to iodine by the enzyme. The copper-containing enzymes may be, for example, a laccase or a bilirubin oxidaze.

11 Claims, 4 Drawing Sheets

5,766,896

METHOD OF PRODUCING IODINE BY USE OF A COPPER CONTAINING OXIDASE ENZYME

FIELD OF THE INVENTION

The present invention relates to a method for oxidation of iodide. More specifically, the invention relates to the use of copper-containing oxidases, particularly laccases, in the oxidation of iodide.

BACKGROUND OF THE INVENTION

Iodine($I_2$) has for many years been widely used as a disinfectant, for many types of situations. Skin cleansers, wound disinfection, contact lens cleaning and water sanitation are just a few of the uses to which iodine has been applied. In addition, iodine is also useful in catalysts, as an animal feed additive, in pharmaceuticals, and as polymer precursor additives. Although the $I_2$-based system of disinfection is extremely effective, several factors limit the scope of directly applying $I_2$. In particular, the production, storage, transportation and handling of $I_2$ are extremely hazardous, due to the chemicals involved in production and also due to the toxicity of $I_2$ itself even in moderate concentrations. Generally, $I_2$ is obtained from natural sources, such as brine, by processes that utilize strong inorganic acids, chlorine gas, and other hazardous chemicals. Iodophores have been developed as $I_2$ carriers to replace simple $I_2$ solutions for industrial and domestic disinfection. In addition, binary systems capable of generating $I_2$ from an $I^-$ salt and a chemical oxidant are also available. Both these systems create the need for disposal of large, potentially toxic amounts of by-products. Another alternative to both industrially producing $I_2$ on a large scale, and to applying $I_2$ as a disinfectant, has been found in the peroxidase-based generation of $I_2$ (U.S. Pat. Nos. 4,282,324; 4,617,190;4,588,586; 4,937,072; 5,055,287;5,227,161; 5,169,455;4,996,146; 4,576,817). Such methods involve the use of the enzyme peroxidase, the oxidizing agent $H_2O_2$, and a source of ionic iodide. Unfortunately, this method has the disadvantage of requiring the hazardous and volatile peroxide or peracid, which has to be either transported or generated in Situ by additional enzymatic or chemical steps, thus making the system more complex and/or costly.

There thus still exists a need for a method of iodine production which avoids the necessity for dealing with harmful chemicals either in the plant or in situ and yet efficiently produces sufficient quantities of the desired product. The present invention now provides a means for achieving this.

SUMMARY OF THE INVENTION

The present invention relates to a method for the production of iodine. The method comprises contacting, in an aqueous solution, a copper-containing oxidase enzyme and a source of ionic iodide($I^-$), for a time and under conditions sufficient to permit the conversion of ionic iodide to iodine by the enzyme. In a preferred embodiment, the enzyme is either a laccase or bilirubin oxidase. In another preferred embodiment, the method is also carried out in the presence of a substrate with high affinity for the copper-containing enzyme. The substrate acts as a mediator, shuttling electrons in the reaction, thereby enhancing the speed at which oxidation of $I^-$ takes place. In using laccase or bilirubin oxidase, the substrate ABTS is a particularly useful mediator in the oxidation process.

BRIEF DESCRIPTION OF THE DRAWINGS

FIG. 1 illustrate double reciprocal plots for recombinant *Myceliophthora thermophila* laccase (r-MtL) catalyzed $I^-$ oxidation.

FIG. 2 illustrates ABTS-assisted, rMtL-catalyzed $I^-$ oxidation.

DETAILED DESCRIPTION OF THE INVENTION

Figure 1A:
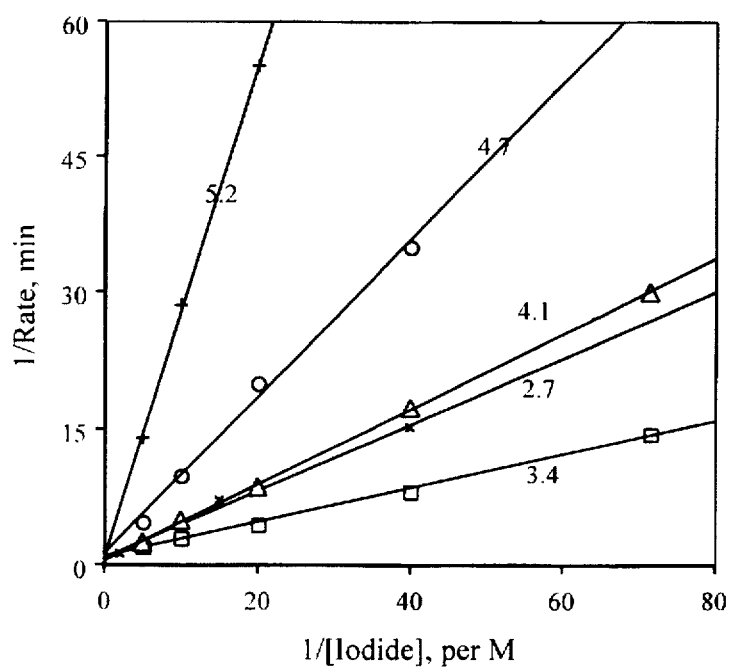
FIG. 1A: correlations between initial rates and $I^-$ concentrations at various pH with 14 µM r-MtL.

It has been well documented that certain halide molecules are capable of inhibiting laccases. Specifically, the inhibition of tree and fungal laccases by fluoride($F^-$) has been described (Koudelka and Ettinger, J. Biol. Chem. 263: 3698–3705, 1988), as well as inhibition of fungal laccases by bromide ($Br^-$) and chloride ($Cl^-$) (Naki and Varfolomeev, Biokhimya 46:1694–1702, 1981). It is presumed that these halides interact with the laccase Type II Cu site resulting in an interruption of electron transfer from Type I site to dioxygen site. There has not previously been any report on the interaction of laccase with iodide($I^-$). As the inhibition potency of the halides is inversely related to the size of the ionic radius, it would be expected that $I^-$, with the largest ionic radius, would have a weak inhibitory effect on laccase. However, it is quite surprising to find that $I^-$ in fact acts as a substrate by surrendering an electron to Type I Cu.

The observation that $I^-$ can act as a laccase substrate has led to the development of a method by which $I^-$ is oxidized to elemental iodine by use of a laccase, or other Cu-containing oxidase enzymes. In an aqueous solution, in which a source of ionic iodide is provided, laccase slowly converts the $I^-$ to $I_2$. The conversion requires no dangerous or volatile chemicals such as chlorine. The source of ionic iodide may be any of the currently known sources, such as alkali metal salts in binary iodine disinfectants, raw or initially iodine harvested brine solutions, bittern, ionic iodide solutions in which iodate from caliche is reduced to iodide, or seaweed. In the case in which chloride is inhibitory to the enzyme used, residual chloride in the starting material should first be reduced to below the inhibition constant. In the case of the Myceliophthora laccase, the inhibition constant is approximately 70 mM.

The enzyme employed in the present process can be any one of a variety of Cu-containing oxidase enzymes. As the following examples show, although laccase is the most active in $I^-$ oxidation, there are other similar enzymes which also provide qualitatively similar activity, albeit in many cases at considerably lower levels than laccase. In particular, bilirubin oxidase exhibits activity which is essentially equivalent to that of laccase. However, other copper containing enzymes tested, such as tyrosinase and ceruloplasmin, also show some level of activity, indicating that the utility is not limited to laccase.

Copper-containing oxidases are obtainable from a wide variety of plant, fungal, bacterial and animal sources, and many are commercially available. In addition to those enzymes listed above, this also includes polyphenol oxidase, ferroxidase II, phenoxazinone synthase, glycerol oxidase, and cytochrome oxidase. The preferred oxidase, laccase, is available from a number of species, particularly fungal species, for example, Aspergillus, Neurospora, Podospora, Botrytis, Collybia, Fomes, Lentinus, Pleurotus, Trametes, Rhizoctonia (U.S. Ser. No. 08/172,331, incorporated herein by reference), Coprinus, Psatyrella, Myceliophthora (U.S. Ser. No. 08/253,781, incorporated herein by reference), Scytalidium (U.S. Ser. No. 08/253,784, incorporated herein by reference), Polyporus (U.S. Ser. No. 08/265,534, incorporated herein by reference), Phlebia (WO 92/01046), and Coriolus (JP 2-238885). Additionally, bilirubin oxidase is readily available from *Myrothecium verrucaria* and *Trachyderma tsunodae*.

The reaction is conducted in an aqueous solution. The enzyme may be free, in pure or crude form, or immobilized on an organic or inorganic support by any means known in the art, e.g., polyacrylamide, cellulose, glass beads, agarose, dextran, methacrylic-based polymers, or ethylenemaleic acid copolymers. Reactions with immobilized enzymes can be conducted in tanks or in columns. The reaction may also be conducted with microbial cells which produce the enzyme.

The aqueous solution is buffered to a pH which provides optimal activity for the enzyme being used, and thus, the preferred pH of the solution will vary depending upon the enzyme used. The pH is maintained in the preferred range by use of an appropriate buffering agent. Such buffers include sodium or potassium phosphate, gluconate, citrate, formate or acetate buffers. The amount of enzyme used will also vary depending on the identity of the enzyme used, but will generally be in the nM to µM range. The amount of $I^-$ used in the reaction mixture should preferably be at or higher than mM levels. The reaction may be conducted at a temperature of between about 15°–50° C., but is preferably conducted at a temperature of about 20°–30° C.

In a preferred embodiment of the present method, the reaction as described above is conducted in the presence of a mediator which accelerates the rate of conversion of $I^-$ to $I_2$. Although copper-containing enzymes such as laccase do oxidize $I^-$, the turnover is usually slow due to low affinity. Therefore, a compound which has high affinity toward the enzyme, and which can act as an intermediary by shuttling of electrons between the enzyme and $I^-$, can improve the efficiency of the reaction. For example, as shown in the examples below, the compound 2,2'-azinobis-(3-ethylbenzthiazoline-6-sulfonic acid) (ABTS), which is a known, and excellent, substrate for laccase and bilirubin oxidase, greatly enhances the efficiency of the oxidation of $I^-$. Although ABTS may not be useful in enhancing the rate of reaction with the other copper-containing enzymes, such as tyrosinase and ceruloplasmin, since it is not an excellent substrate for these enzymes, alternate mediators which are more suitable substrates may be used with these enzymes. The important factors in choosing alternate mediators for any given enzyme is that the mediator be a good substrate for the enzyme, and that it have a similar or higher redox potential than $I^-$. Examples of additional mediators which should be useful for reactions utilizing enzymes other than laccase and bilirubin oxidase are phenolics, heterocyclic compounds, hydroquinones, and free or coordinated chelated transition metal ions(i.e., $Fe^{2+}$, $Fe(bipyridyl)_2^{2+}$, $Ru(CN)_6^{4-}$, and the like. The amount of mediator will differ depending upon the identity of the compound used, and its suitability based on the stated favorable characteristics; for ABTS, which is an ideal mediator for laccase and bilirubin oxidase when judged by the stated criteria, only a small amount, about 0.1 mM, is required to enhance the reaction $10^3$-fold over the results observed in the absence of ABTS. For any given mediator, the concentration used depends on its $K_m$ for the enzyme being used, which value is routinely determinable by one of ordinary skill in the art.

The iodine produced in the course of the reaction may be recovered by any suitable means, such as filtration/centrifugation, inert gas blow-out, and immiscible organic solvent extraction.

The invention is further illustrated by the following non-limiting examples.

EXAMPLES

I. MATERIALS AND METHODS

A. Materials

Chemicals used as buffers and substrates are commercial products of at least reagent grade. Ascorbate oxidase (Cucurbita species), ceruloplasmin (porcine plasma), bilirubin oxidase (*Myrothecium verrucaria*) and tyrosinase (mushroom) are purchased from Sigma and used as received. The contents of the enzymes in lyophilized powder or solution are confirmed by uv-visible absorption and published extinction coefficients. The stated activity of ascorbate oxidase is confirmed with ascorbic acid.

B. Methods

Recombinantly produced *Myceliophthora thermophila* laccase ((r-MtL; described in copending U.S. Ser. No. 08/278,473, the contents of which are incorporated herein by reference) is purified and the activity is determined by syringaldazine and 2,2'-azinobis-(3-ethylbenzothiazoline-6-sulfonic acid) (ABTS) oxidations as follows: Syringaldazine oxidation is carried out at 30° C. in a 1-cm quartz cuvette. 60 µl syringaldazine stock solution (0.28 mM in 50% ethanol) and 20 µl sample are mixed with 0.8 ml preheated buffer solution. The oxidation is monitored at 530 nm over 5 minutes. ABTS oxidation assays are done using 0.4 mM AsTS, B&R buffer at various pHs, at room temperature by monitoring absorbance change at 418 nm. The extinction coefficient of 36 $mM^{-1}cm^{-1}$ is used to calculate the rate. Spectroscopic assays are conducted on either a spectrophotometer (Shimadzu UV160) or a microplate reader (Molecular Devices). Britton & Robinson (B & R) buffers are prepared according to a standard protocol (Quelle, Biochemisches Taschenbuch, H. M. Raven, II. Teil, S.93 u. 102, 1964).

Enzymatic assays for determining oxidation of $I^-$ are conducted in B & R buffer containing from 1–20 nM MtL (subunit concentration) and 10 to 200 mM NaI at 20° C. for 5–10 minutes. The extinction coefficient of 26 $mM^{-1}cm^{-1}$ is used to calculate rate. Oxidation of $I^-$ is spectrally monitored at 340 or 353 nm and the spectrum of the oxidation product is found identical to that of $I_3^-$-(Hosoya, Biochem. (Tokyo) 53: 381, 1963). Kinetic parameters are extracted by a non-linear regression fitting (Prism, GraphPad) of rate and concentration data to the equation of rate=$V_{max}$*|substrate|/$K_m$+|substrate|.

Ascorbate oxidase, ceruloplasmin, bilirubin oxidase, and tyrosinase at concentrations up to µM level are also tested under similar conditions for $I^-$ oxidation catalysis.

II. RESULTS

Catalyses for $I^-$ oxidation by rMtL and other Cu-containing enzymes—In aerated solution, $I^-$ can be slowly oxidized to $I_2$. When $I^-$ (in the form of NaI) is in excess, $I_3^-$ is formed reversibly from $I^-$ and $I_2$ to give a characteristic spectrum with a band centered around 353 (Hosoya, supra). r-MtL can accelerate the process; around pH 3, the catalyzed $I^-$ oxidation can be many orders faster than the non-enzymatic $I^-$ oxidation.

Figure 1B:
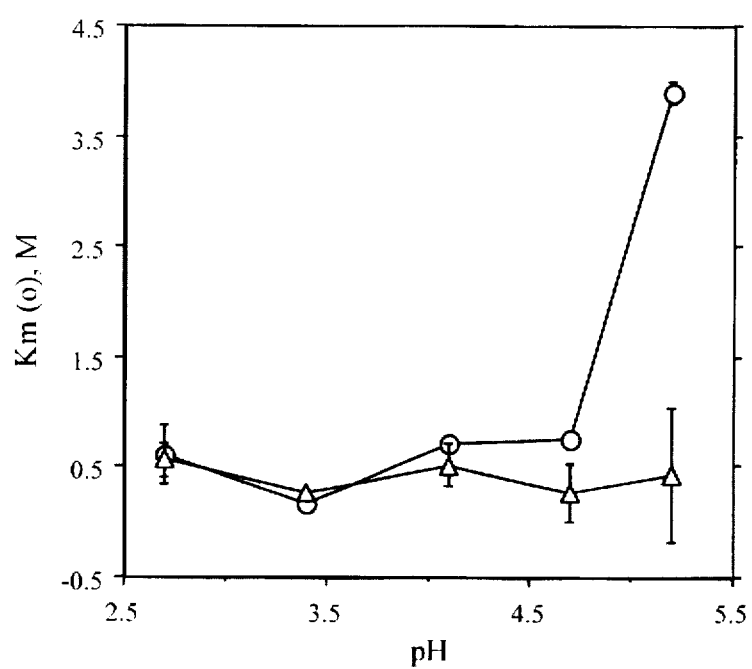
FIG. 1B: Dependencies of $K_m$ and $V_{max}$ (extracted from FIG. 1A) on pH.

The reciprocals of the initial rates of $I_2$ formation and the $I^-$ concentration exhibit typical linear correlation (FIG. 1A). Over the tested range of 1–15 µM, the maximal initial rates are proportional to concentration of r-MtL. The activity is optimal at pH 3.4. Above pH 6, the reaction is minimal. As a substrate I⁻ shows an apparent $K_m$ dependent on pH. The smallest $K_m$, 0.16±0.02M, is found at pH 3.4. The pH dependence of $V_{max}$ is less significant (FIG. 1B). At pH 3.4, a $V_{max}$ of 2.7±0.2 turnover per minute is found. I⁻ is not as good a substrate for r-MtL as syringaldazine, whose $K_m$ and $V_{max}$ at optimal pH(7) are at about 10 μM and about 400 turnover per minute levels, respectively.

At pH 5, ascorbate oxidase at concentrations up to 1.5 μM shows an activity of lower than 0.1 turnover per minute. At μM level, ceruloplasmin shows negligible catalysis in I⁻ oxidation with 0.1M NaI at pH 6 (ca. 0.1 turnover per minute). As an I⁻ oxidase, tyrosinase has a pH-activity profile in which the relative activity at pH 4.1,5.2, 6.0 and >7 is ~58,33,10 and <5% of that at pH 2.7, respectively. At its optimal pH of 2.7, tyrosinase catalyzes I⁻ oxidation with a $K_m$ of ~0.1M and a $V_{max}$ of ~0.1 turnover per minute. Initial I⁻ oxidation rates are proportional to tyrosinase concentration over a range of 2 to 20 μM. As an I⁻ oxidase, bilirubin oxidase has a pH activity profile in which the relative activity at pH 2.7, 5.2, 6.0, 7.0, 8.2, and >9 is ~95, 91, 80, 59, 32, and <6% of that at pH 4.1, respectively. At its optimal pH of 4.1, bilirubin oxidase catalyzes I⁻ with a $K_m$ of ~0.15±0.03M and a $V_{max}$ of 1.7±0.1 turnover per minute. Initial rates are proportional to bilirubin oxidase concentration over the range of 0.5–5 μM.

Catalysis for ABTS oxidation—At pH 5, ascorbate oxidase at concentrations up to 1.5 μM shows no activity in oxidation of ABTS. The rates of tyrosinase-catalyzed ABTS oxidation are proportional to tyrosinase concentration over the range of 0.2–2 μM tested. Tyrosinase has an optimal activity at pH 2.7, from which a $K_m$ of 0.18±0.01 mM, and a $V_{max}$ of 3.1±0.1 turnover per minute were found. Initial rates of ceruloplasmin-catalyzed ABTS oxidation are proportional to a ceruloplasmin concentration over the range of 0.1 to 1 μM tested. Ceruloplasmin has an optimal ABTS oxidase activity at pH 4.1, from which a $K_m$ of 0.11±0.04 mM and a $V_{max}$ of 9.3±1.3 turnover per minute are found. Initial rates of bilirubin oxidase-catalyzed ABTS oxidation are proportional to oxidase concentration over the range of 1–10 nM tested. The pH profile shows an optimal pH of 4.1, from which a $K_m$ of 0.12±0.01 mM and a $V_{max}$ of (1310±40) turnover per minute are found. rMtL has a pH activity profile with an optimal pH$\leq$2.7. At pH 4.1, ABTS has a $K_m$ of 5.6±0.5 μM and a $V_{max}$ of 1460±31 turnover per minute are found.

Figure 2A:
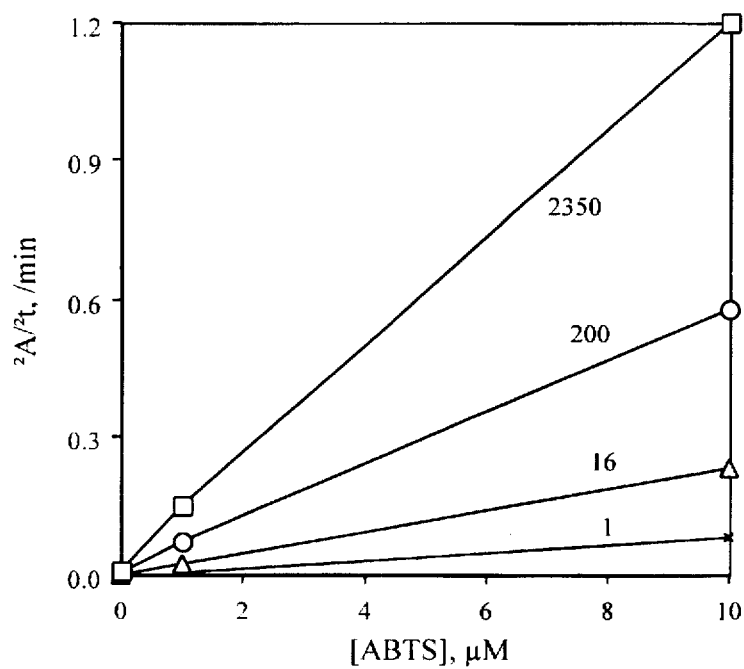
FIG 2A: Dependence of initial $I^-$ oxidation rates on ABTS and r-MtL (nM) concentrations.

ABTS-assisted catalyses—Oxidized ABTS (ABTS⁺), prepared by preincubation with laccase, readily oxidizes I⁻. In the presence of minute amounts of ABTS, the laccase catalyzed I⁻ oxidation can be greatly enhanced (FIG. 2A). Kinetic analysis demonstrates that the rate limiting step resides with the oxidation of ABTS by laccase.

Figure 2B:
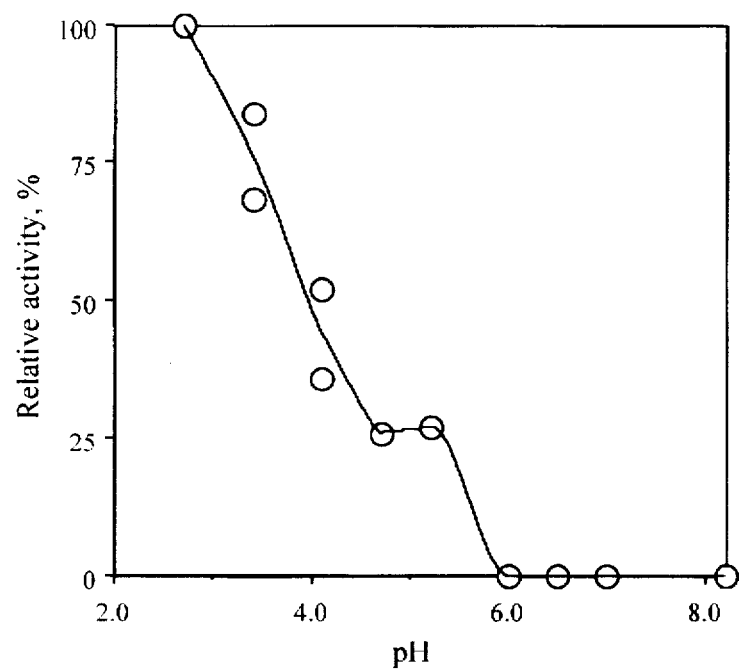
FIG. 2B: pH profile of initial $I^-$ oxidation rate with 2.4 nM r-MtL and 10 µM ABTS.

When both ABTS and I⁻ are present at sufficient levels, only the spectrum of $I_3^-$ is detected as long as I⁻ remains in excess to ABTS. When all the I⁻ is consumed, the spectrum of oxidized ABTS emerges. In ABTS-assisted enzymatic catalysis of I⁻ oxidation, the pH-activity profile (FIG. 2B) is similar to that for rMtL-catalyzed ABTS oxidation (optimal pH shifted from 3.4 to $\leq$2.7). The apparent $K_m$ and $V_{max}$ (6.4±0.8 μM and 860±40 turnover per minute) extracted from the dependence of I⁻ oxidation rates on ABTS concentration are close to that of r-MtL-catalyzed oxidation of ABTS itself.

Due to their poor ABTS oxidase activities, ascorbate oxidase, ceruloplasmin, and tyrosinase all show negligible ABTS-assisted catalysis for I⁻ oxidation. When ABTS is included in bilirubin oxidase-catalyzed I⁻ oxidation, an activity optimum at pH 4.1 is observed. At this pH, an apparent $K_m$ of 0.18±0.02 mM and a $V_{max}$ of 600±40 turnover per minute is observed for I⁻ oxidation. These kinetic parameters, being close to that for oxidase-catalyzed ABTS oxidation itself, indicate the rate-limiting step in the assisted catalysis is the oxidation of ABTS.

Discussion—There have been no previous reports describing I⁻ oxidase activity of laccase or oxidase-catalyzed I⁻ oxidation. Although it is known that F⁻, and probably also Cl⁻ and Br⁻, binds to Type II Cu in laccase, the observed catalysis of laccase in I⁻ oxidation implies that I⁻ must interact with Type I Cu. The redox potentials (versus Normal Hydrogen Electrode (NHE)) of Type I Cu are in the range of 480 to 530 mV vs NHE for r-MtL and bilirubin oxidase; and about 800 mV for Polyporus laccase (Reinhammar, Biochim. Biophys. Acta 275:245–259, 1972). The potential for ABTS⁺/ABTS couple is about 700 mV. These potentials are close to or higher than that of $I_3^-/I^-$ couple (540 mV), thus making I⁻ oxidation by Type I Cu or ABTS⁺ thermodynamically feasible.

Although I⁻ could be potentially a stronger reductant than ABTS, kinetic factors make the former much less reactive toward laccase. As a substrate, ABTS has an ~10³-fold smaller $K_m$ and an ~10³-fold larger $V_{max}$ in comparison with I⁻. Because oxidized ABTS apparently exchanges electrons freely with I⁻ in solution, electron-shuttling by ABTS between I⁻ and laccase enhances greatly laccase-catalyzed I⁻ oxidation. Since the rate-limiting step is at the oxidation of ABTS, it is possible to regulate the catalysis for I⁻ oxidation by the concentration of ABTS or other suitable mediators.

Among the Cu-containing enzymes tested, bilirubin oxidase functions quantitatively similarly to laccase, while the other enzymes tested perform the direct oxidation of I⁻ less efficiently. Since ABTS itself is not an excellent substrate for ascorbate oxidase, ceruloplasmin, and tyrosinase, only a minor effect from ABTS in assisting I⁻ oxidation catalyzed by these enzymes would be expected. However, other materials which are good substrates for these enzymes, such as suitable phenolics, hydroquinones, heterocyclic compounds, and free or chelated transition metal ions can be used as alternate mediators with these enzymes for I⁻ oxidation.

What is claimed is:

1. A method for producing iodine which comprises:

(a) contacting, in an aqueous solution, a copper-containing fungal laccase or fungal bilirubin oxidase and a source of ionic iodide (I–), under conditions sufficient to permit the conversion of the ionic iodide to iodine by the laccase; and (b) recovering the iodine from the aqueous solution.

2. The method of claim 1 in which the laccase is selected from the group consisting of a Myceliophthora laccase, a Scytalidium laccase, a Polyporus laccase, and a Rhizoctonia laccase, an Aspergillus laccase, a Neurospora laccase, a Podospora laccase, a Botrytis laccase a Collybia laccase, a Fomes laccase, a Lentinus laccase, a Pleurotus laccase, a Trametes laccase, a Coprinus laccase, a Psatryella laccase, a Phlebia laccase, and a Coriolus laccase.

3. The method of claim 1 in which the laccase is a Myceliophthora laccase, a Scytalidium laccase, a Polyporus laccase, or a Rhizoctonia laccase.

4. The method of claim 1 in which the laccase is a Myceliophthora laccase.

5. The method of claim 1 in which the bilirubin oxidase is a Myrothecium or a Trachyderma bilirubin oxidase.

6. The method of claim 1 in which the enzyme is Myrothecium bilirubin oxidase.

7. The method of claim 1 which is conducted in the presence of a mediator.

8. The method of claim 7 in which the mediator is 2,2'-azinobis-(3-ethylbenzthiazoline-6-sulfonic acid.

9. A method for oxidation of iodide which comprises contacting, in an aqueous solution, a fungal laccase or a bilirubin oxidase and a source of ionic iodide ($I^-$), in the presence of mediator, for a time and under conditions sufficient to permit the conversion of ionic iodide to iodine by the laccase; and recovering the iodine from the aqueous solution.

10. The method of claim 9 which is conducted in the presence of a mediator which accelerates the conversion of ionic iodide to iodine by the fungal laccase or fungal bilirubin oxidase.

11. The method of claim 10 in which the mediator is 2,2'-azinobis-(3-ethylbenzthiazoline-6-sulfonic acid.

* * * * *